United States Patent
Wheeler et al.

(10) Patent No.: US 12,138,045 B2
(45) Date of Patent: Nov. 12, 2024

(54) IN-VEHICLE HEARING TEST

(71) Applicant: Ford Global Technologies, LLC, Dearborn, MI (US)

(72) Inventors: Joshua Wheeler, Trenton, MI (US); Pietro Buttolo, Dearborn Heights, MI (US); Cynthia M. Neubecker, Westland, MI (US); Thomas Chrapkiewicz, Farmington Hills, MI (US); David Graham Smith, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 918 days.

(21) Appl. No.: 17/155,265

(22) Filed: Jan. 22, 2021

(65) Prior Publication Data
US 2022/0233105 A1    Jul. 28, 2022

(51) Int. Cl.
*A61B 5/12* (2006.01)
*A61B 5/00* (2006.01)
(Continued)

(52) U.S. Cl.
CPC ............. *A61B 5/123* (2013.01); *H03G 3/32* (2013.01); *H04S 7/303* (2013.01); *H04R 2499/13* (2013.01)

(58) Field of Classification Search
CPC ........... A61B 5/121; A61B 5/38; A61B 5/123; A61B 5/1114; A61B 5/7415; A61B 5/0077; A61B 5/746; A61B 5/7475; A61B 5/6893; A61B 5/12–125; A61B 5/1116; A61B 5/7203–7207; A61B 2503/22; H04R 25/305; H04R 29/001;
(Continued)

(56) References Cited

U.S. PATENT DOCUMENTS 4,641,344 A * 2/1987 Kasai ................... H03G 3/3005
                                                    381/86
10,368,154 B2 * 7/2019 Blau ..................... A61B 5/0022
(Continued)

FOREIGN PATENT DOCUMENTS

DE    102009022685 A1 * 12/2010 ............... H04R 5/02
DE    102014210606 A1    12/2015
(Continued)

OTHER PUBLICATIONS

English Translation of DE-102015015425-A1, Burmester Audiosysteme De GmbH, 5 pages, printed on Nov. 30, 2023, (Year: 2017).*
(Continued)

*Primary Examiner* — Matthew Kremer
*Assistant Examiner* — Jennifer Grace Baires-Tweed
(74) *Attorney, Agent, or Firm* — Frank Lollo; Bejin Bieneman PLC (57) ABSTRACT

A system includes a computer including a processor and a memory storing instructions executable by the processor to detect a position of a head of an occupant within a passenger compartment of a vehicle. The instructions include instructions to conduct a hearing test based on the position of the head of the occupant. The instructions include instructions to output sound at least at one of a specified frequency or amplitude, the specified frequency or amplitude selected based on results of the hearing test.

20 Claims, 4 Drawing Sheets

(51) Int. Cl.
*A61B 5/11* (2006.01)
*H03G 3/32* (2006.01)
*H04S 7/00* (2006.01)

(58) Field of Classification Search
CPC ......... H04R 2499/10–13; G16H 50/30; G16H 10/60; H03G 3/32; H04S 7/303; H04S 2400/13; H04S 7/00–40
See application file for complete search history.

(56) References Cited

U.S. PATENT DOCUMENTS

| | | | |
|---|---|---|---|
| 2016/0166181 A1* | 6/2016 | Shennib | H04R 25/305 |
| | | | 600/559 |
| 2019/0281402 A1 | 9/2019 | Schmidt et al. | |
| 2020/0066070 A1 | 2/2020 | Wells | |

FOREIGN PATENT DOCUMENTS

| | | | | | |
|---|---|---|---|---|---|
| DE | 102015015425 A1 | * | 6/2017 | | |
| GB | 2557178 A | * | 6/2018 | ............. | B60K 35/00 |
| JP | 2008125587 A | * | 6/2008 | | |
| WO | WO-2020035198 A1 | * | 2/2020 | | |

OTHER PUBLICATIONS

English Translation of DE 102009022685 A1, Bayerische Motoren Werke AG, 7 pages, printed on Nov. 30, 2023, (Year: 2010).*
English Translation of JP 2008125587 A, Baisera KK Mimy Electronics Co Ltd, 16 pages, printed on May 24, 2024, (Year: 2008).*
English Translation of WO 2020035198 A1, Volkswagen Aktiengesellschaft, 6 pages, printed on Sep. 18, 2024,. (Year: 2020).*

* cited by examiner

IN-VEHICLE HEARING TEST

BACKGROUND

Hearing tests are generally conducted by hearing institutes or laboratories, and are performed using specialized medical devices such as audiometers, special headphones and sealed rooms. The most common type of audiometer generates pure tones, with varying amplitudes as chosen by a human operator, typically a hearing specialist, and delivered to the subject's ears through the headphones. During testing, the subject indicates that a tone was heard by pressing a feedback button or by a visual signal to the operator. The audiometer enables the operator to produce an audiogram, describing the subject's hearing acuity.

DETAILED DESCRIPTION

A system includes a computer including a processor and a memory storing instructions executable by the processor to detect a position of a head of an occupant within a passenger compartment of a vehicle. The instructions include instructions to conduct a hearing test based on the position of the head of the occupant. The instructions include instructions to output sound at least at one of a specified frequency or amplitude, the specified frequency or amplitude selected based on results of the hearing test.

The instructions may include instructions to select a first amplitude of sound for conducting the hearing test, the first amplitude of sound being determined based on the position of the head.

The instructions may include instructions to select a second amplitude of sound for conducting the hearing test, the second amplitude of sound being determined based on the position of the head and different than the first amplitude of sound.

The instructions may include instructions to output the first amplitude of sound at a right side of the passenger compartment and the second amplitude of sound at a left side of the passenger compartment.

The instructions may include instructions to display, via a human machine interface in the vehicle, the position of the head and a specified head position, and to conduct the hearing test while the position of the head matches the specified head position.

The instructions may include instructions to conduct the hearing test while the position of the head matches a specified head position.

The instructions may include instructions to detect the position of the head based on data from a camera.

The instructions may include instructions to conduct the hearing test in response to determining an ambient noise level in the passenger compartment is below a predetermined threshold.

The instructions may include instructions to conduct the hearing test in response to determining an ambient noise level in the passenger compartment has been below a predetermined threshold for a specified amount of time.

The instructions may include instructions to estimate the ambient noise level in the passenger compartment based on a speed of the vehicle.

The instructions may include instructions to store results of a plurality of hearing tests and to notify the occupant when the results of the plurality of hearing tests indicate deterioration of hearing of the occupant.

The instructions may include instructions to limit an amplitude of sound output in the passenger compartment based on the results of the hearing test.

The instructions may include instructions to store and associate the results of the hearing test with a profile of the occupant.

A method includes detecting a position of a head of an occupant within a passenger compartment of a vehicle. The method includes conducting a hearing test based on the position of the head of the occupant. The method includes outputting sound at least at one of a specified frequency or amplitude, the specified frequency or amplitude selected based on results of the hearing test.

The method may include selecting a first amplitude of sound for use while conducting the hearing test, the first amplitude of sound determined based on the position of the head.

The method may include selecting a second amplitude of sound for use while conducting the hearing test, the second amplitude of sound determined based on the position of the head and different than the first amplitude of sound.

The method may include outputting the first amplitude of sound at a right side of the passenger compartment and the second amplitude of sound at a left side of the compartment.

The method may include conducting the hearing test while the position of the head matches a specified head position.

The method may include conducting the hearing test after determining an ambient noise level in the passenger compartment has been below a predetermined threshold for a specified amount of time.

The method may include estimating the ambient noise level in the passenger compartment based on a speed of the vehicle.

The method may include storing results of a plurality of hearing tests and to notify the occupant when the results of the plurality of hearing tests indicate deterioration of hearing of the occupant.

The method may include displaying, via a human machine interface in the vehicle, the position of the head and a specified head position, and to conduct the hearing test while the position of the head matches the specified head position.

The method may include detecting the position of the head based on data from a camera.

The method may include conducting the hearing test in response to determining an ambient noise level in the passenger compartment is below a predetermined threshold.

The method may include limiting an amplitude of sound output in the passenger compartment based on the results of the hearing test.

A memory may store instructions executable by a processor to perform the method.

A system may include a processor and a memory storing instructions executable by the processor to perform the method.

Figure 1:
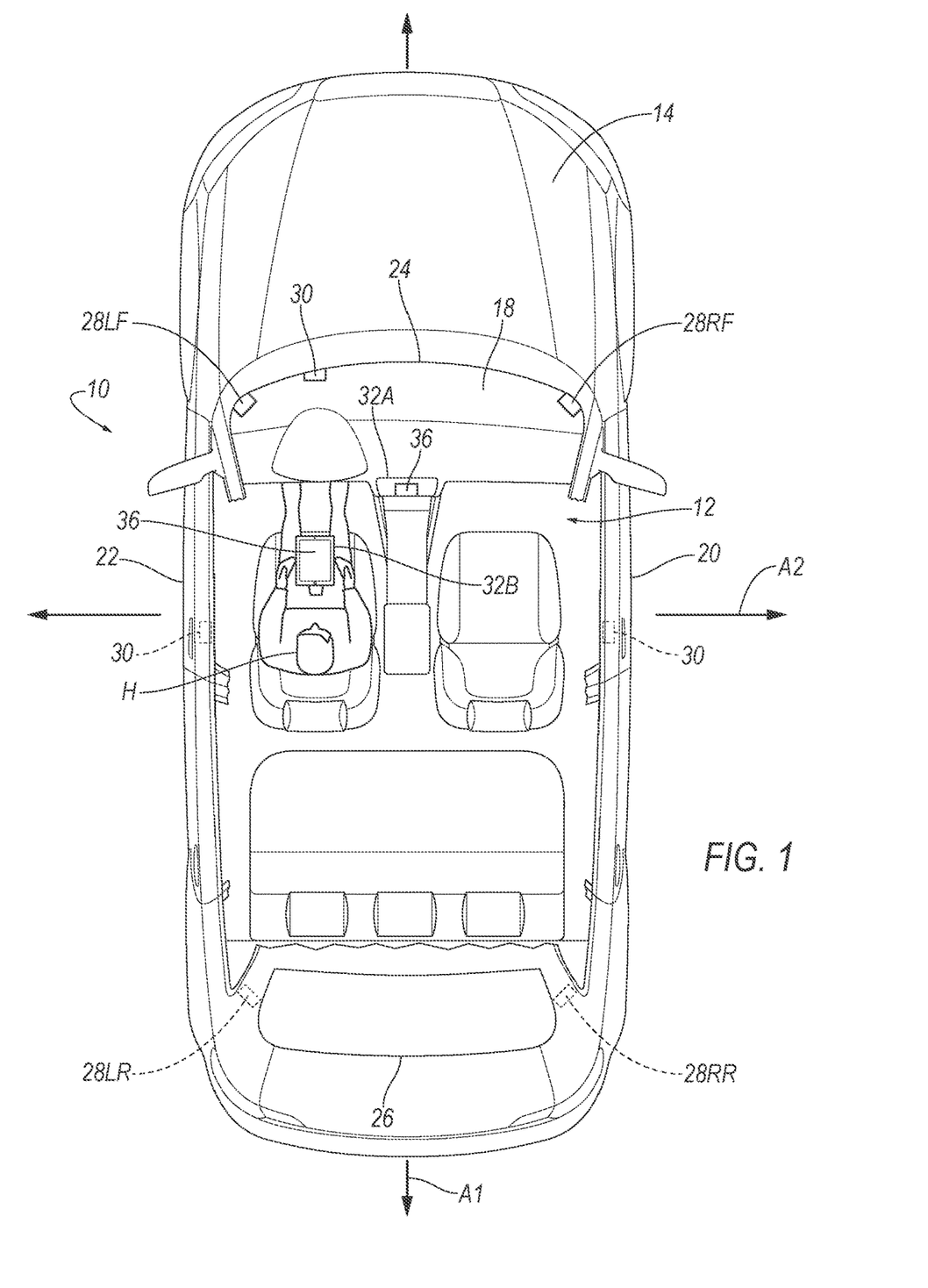
FIG. 1 is a top view of a system for conducting a hearing test in a passenger compartment of a vehicle.
Figure 2:
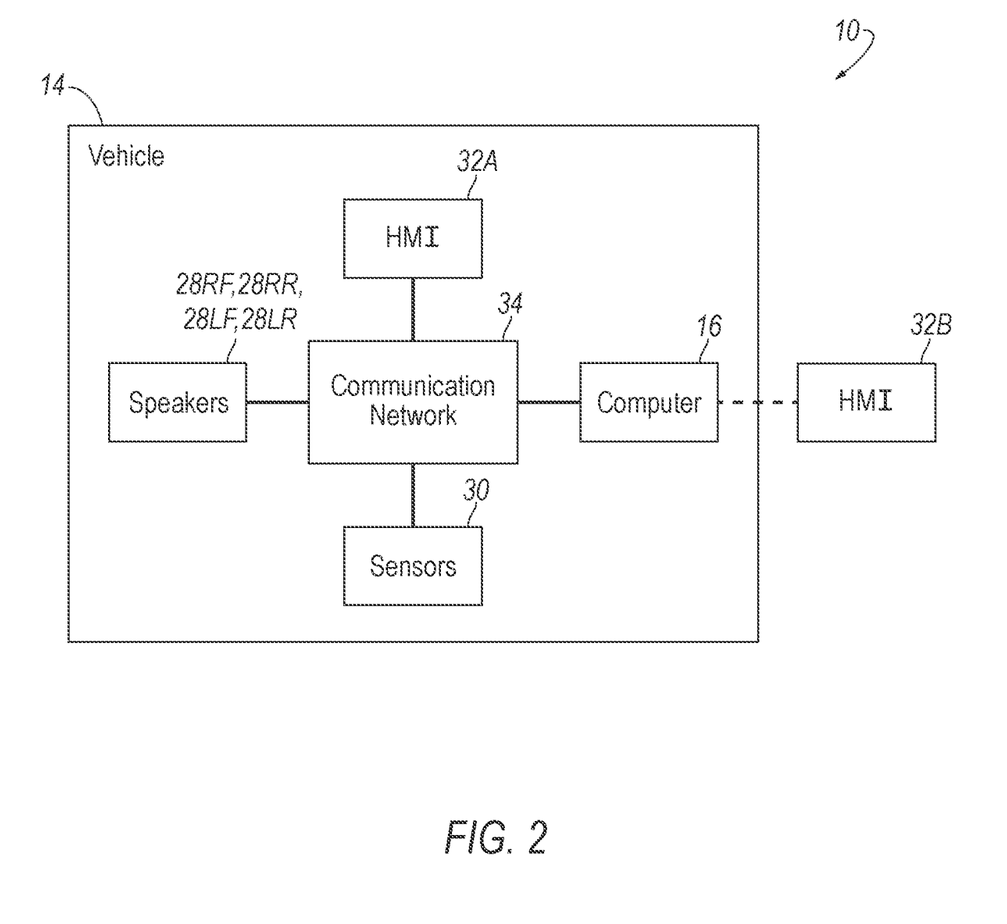
FIG. 2 is a block diagram of the system.

With reference to FIGS. 1 and 2, wherein like numerals indicate like parts throughout the drawings, a system 10 for controlling sound within a passenger compartment 12 of a vehicle 14 is shown. The system 10 comprises a computer 16 including a processor and a memory storing instructions executable by the processor to detect a position of a head H of an occupant within a passenger compartment 12 of a vehicle 14. The instructions include instructions to conduct a hearing test based on the position of the head H of the occupant. The instructions include instructions to output sound at least at one of a specified frequency or amplitude, the specified frequency or amplitude selected based on results of the hearing test.

In the present description, relative vehicular orientations and directions (by way of example, top, bottom, front, rear, outboard, inboard, inward, outward, lateral, left, right, etc.) are from the perspective of an occupant seated in the vehicle 14 facing forward, e.g., toward a forward instrument panel 18 and/or forward windshield of the vehicle 14. The forward direction of the vehicle 14 is the direction of movement of the vehicle 14 when the vehicle 14 is engaged in forward drive with wheels of the vehicle 14 straight.

Conducting the hearing test based on the position of the head H of the occupant provides more robust and accurate hearing test results, e.g., compared to a hearing test conducted without information indicating the position of the head H of the occupant. For example, a sound output at a right side 20 of the vehicle 14 may be more perceptible to the occupant when seated at the right side 20 than at a left side 22 of the vehicle 14, and vice versa. Conducting the hearing test based on the position of the head H enables this difference in perception to be accounted for to achieve more accurate hearing test results.

The vehicle 14 may be any suitable type of automobile, e.g., a passenger or commercial automobile such as a sedan, a coupe, a truck, a sport utility, a crossover, a van, a minivan, a taxi, a bus, etc. The vehicle 14, for example, may be autonomous. In other words, the vehicle 14 may be autonomously operated such that the vehicle 14 may be driven without constant attention from a driver, i.e., the vehicle 14 may be self-driving without human input.

The vehicle 14 defines the passenger compartment 12. The passenger compartment 12 houses occupants, if any, of the vehicle 14. The passenger compartment 12 may extend across the vehicle 14, i.e., from the right side 20 to the left side 22 of the vehicle 14. The passenger compartment 12 includes a front end 24 and a rear end 26 with the front end 24 being in front of the rear end 26 during forward movement of the vehicle 14.

The vehicle 14 defines a longitudinal axis A1 extending between the front and the rear of the vehicle 14. The vehicle 14 defines a cross-vehicle axis A2 extending between the right side 20 and the left side 22 of the vehicle 14. The longitudinal axis A1 and the cross-vehicle axis A2 are perpendicular relative to each other. The longitudinal axis A1 and the cross-vehicle axis A2 are generally shown extending through a center of the vehicle 14, however, the longitudinal axis A1 and the cross-vehicle axis A2 do not necessarily define lateral or cross-vehicle centers.

The vehicle 14 may include one or more speakers 28RF, 28RR, 28LF, 28LR that can convert an electrical signal to sound, i.e., each speaker 28RF, 28RR, 28LF, 28LR may include a transducer that converts the electric signal to vibrations to generate sound at a desired frequency. Each speaker 28RF, 28RR, 28LF, 28LR can receive the electrical signal from an audio amplifier. The audio amplifier, as is known, can amplify an electric signal provided to drive one or more of the speakers 28RF, 28RR, 28LF, 28LR. The amplifier can be used to control amplitude of a signal, e.g., amplitude of a sound (e.g., in decibels) of a sound to be output by the speakers 28RF, 28RR, 28LF, 28LR. One or more of the speakers 28RF, 28RR, 28LF, 28LR may be actuated to generate sound, e.g., in response to a command from the computer 16. The speakers 28RF, 28RR, 28LF, 28LR may be supported by the vehicle 14 at various positions within the passenger compartment 12. For example, a right-front speaker 28RF supported at the right side 20 and the front end 24, a right-rear speaker 28RR supported the right side 20 and the rear end 26, a left-front speaker 28LF supported at the left side 22 and the front end 24, and a left-rear speaker 28LR supported at the left side 22 and the rear end 26.

The vehicle 14 includes sensors 30 that can obtain one or more measurements of one or more physical phenomena. Often, but not necessarily, a sensor includes a digital-to-analog converter to converted sensed analog data to a digital signal that can be provided to a digital computer, e.g., via a network. Sensors 30 can include a variety of devices, and can be disposed to sense an environment, provide data about a machine, etc., in a variety of ways. For example, sensors 30 could include cameras, short range radar, long range radar, LIDAR, and/or ultrasonic transducers, weight sensors, accelerometers, motion detectors, etc., i.e., sensors 30 to provide a variety of data. To provide just a few non-limiting examples, sensor data could include data for determining a position of a component, a location of an object, a speed of an object, a type of an object, a slope of a roadway, a temperature, an presence or amount of moisture, a fuel level, a data rate, etc. The sensors 30 may provide sensor data to the computer 16.

One or more of the sensors 30 may be vehicle speed sensors that output a vehicle speed, i.e., a rate of movement of the vehicle 14, typically in the forward direction, with respect to a ground surface such as a road. For example, one or more wheel speed sensors can be provided as is known to detect a rate of rotation of vehicle wheels, from which a speed of the vehicle 14 can be determined. Alternatively or additionally, a vehicle speed sensor can detect a rate of rotation of a crankshaft, from which the vehicle 14 speed can be determined.

One or more of the sensors 30 may be occupant sensors that detect the position of the head H of the occupant relative to the passenger compartment 12. For example, one or more image sensors may be supported within the passenger compartment 12, e.g., by the instrument panel 18 or the like, and be orientated toward a top portion of one of the seats. An image sensor could include one or more cameras, CCD image sensors, CMOS image sensors, etc. As another example, proximity sensors, such as a capacitive proximity sensor, a photoelectric sensor, an infrared proximity sensor, etc., may be supported by a pillar, roof, etc., and orientated toward a top portion of one of the seats to detect a distance to the head H. Other sensors 30 may be used to detect the position of the head H.

The system 10 can include one or more human-machine-interfaces (HMIs) 32A, 32B. The HMIs 32A, 32B may provide information to, and/or receive information from, the occupant. The HMIs 32A, 32B may include, e.g., one or more of a display, a touchscreen display, a microphone, a speaker, etc. The HMI 32A may be supported by the vehicle 14, e.g., fixed to the instrument panel 18. The HMI 32B may be separate from vehicle 14, e.g., a smart phone, tablet computer, etc., which the occupant may bring into the passenger compartment 12. The HMI 32A, 32B may provide information to, and/or receive information from, the computer 16.

The computer 16 is a microprocessor-based controller implemented via circuits, chips, or other electronic components. The computer 16 includes a processor and a memory such as are known. The memory includes one or more forms of computer readable media, and stores instructions executable by the computer 16 for performing various operations, including as disclosed herein. The computer 16 may be programmed to execute operations disclosed herein. Specifically, the memory stores instructions executable by the processor to execute the operations disclosed herein and electronically stores data and/or databases. For example, the computer 16 may include one or more dedicated electronic circuit including an ASIC (Application Specific Integrated Circuit) that is manufactured for a particular operation. In another example, the computer 16 may include an FPGA (Field Programmable Gate Array) which is an integrated circuit manufactured to be configurable by a customer. As an example, a hardware description language such as VHDL (Very High Speed Integrated Circuit Hardware Description Language) is used in electronic design automation to describe digital and mixed-signal systems such as FPGA and ASIC. For example, an ASIC is manufactured based on VHDL programming provided pre-manufacturing, and logical components inside an FPGA may be configured based on VHDL programming, e.g. stored in a memory electrically connected to the FPGA circuit. In some examples, a combination of processor(s), ASIC(s), and/or FPGA circuits may be included inside a chip packaging. The computer 16 may be a set of computers communicating with one another.

The computer 16 is generally arranged for communications on the communication network 34 that can include a bus in the vehicle 14 such as a controller area network (CAN) or the like, and/or other wired and/or wireless mechanisms. Via the communication network 34, the computer 16 may transmit messages to various devices in the vehicle 14, and/or receive messages (e.g., CAN messages) from the various devices, e.g., the HMI 32A supported on the instrument panel 18, the speakers 28RF, 28RR, 28LF, 28LR, the various sensors 30, etc. Alternatively or additionally, in cases where the computer 16 comprises a plurality of devices, the communication network 34 may be used for communications between devices represented as the computer 16 in this disclosure.

The computer 16 can communicate, typically via a wireless connection, with one or more remote computers that are physically separate, and typically geographically remote, from the vehicle 14, such as communicating with the HMI 32B that is a tablet computer, etc. The computer 16 may provide data to, and receive data from, the remote computers via a network. The network represents one or more mechanisms by which the computer 16 of the vehicle 14 may communicate with the remote computers. Accordingly, the network can be one or more of various wired or wireless communication mechanisms, including any desired combination of wired (e.g., cable and fiber) and/or wireless (e.g., cellular, wireless, satellite, microwave, and radio frequency) communication mechanisms and any desired network topology (or topologies when multiple communication mechanisms are utilized). Exemplary networks include wireless communication networks (e.g., using Bluetooth®, Bluetooth® Low Energy (BLE), IEEE 802.11, Dedicated Short Range Communications (DSRC), etc.), local area networks (LAN) and/or wide area networks (WAN), including the Internet, providing data communication services. The network can be a vehicle-to-everything network (V2X), where "X" signifies an entity with which the computer 16 of the vehicle 14 can communicate with, e.g., a vehicle (V2V), infrastructure (V2I), a pedestrian (V2P), etc. The computer 16 can communicate with one or more devices over the V2X network, e.g., with another vehicle, with a device mounted to infrastructure, to a user device separate from the vehicle 14 (such as the HMI 32B), etc. One example of a V2X network is a cellular-V2X (C-V2X) network. The C-V2X network is a band of frequencies dedicated to V2X communications, e.g., between vehicles, portable devices, etc. For example, the C-V2X network can include frequencies between 5.90 and 5.99 gigahertz (GHz) (e.g., 5.85-5.925 GHz).

The computer 16 is programmed to, i.e., the memory stores instructions executable by the processor to, detect the position of the head H of the occupant within the passenger compartment 12 of the vehicle 14. The detected position of the head H is relative to the passenger compartment 12, e.g., relative to the right side 20, the left side 22, the front end 24, the rear end 26, one or more or the speakers 28RF, 28RR, 28LF, 28LR, etc. The detected position of the head H may be identified as coordinates along the longitudinal axis A1 and/or cross-vehicle axis A2. The computer 16 may detect the position of the head H with data from the sensors 30, e.g., from a camera and/or a proximity sensor. For example, pixels values of image data from a camera fixed relative to the passenger compartment 12 may be analyzed to identify the head H of the occupant in such image data, e.g., using any suitable image analysis technique, e.g., techniques are known for determining an orientation or pose of a part of a human body, e.g., as described in *Face-from-Depth for Head Pose Estimation on Depth Images* dated 12 Dec. 2017 and other papers available at https://paperswitcode.com/task/head-pose-estimation/codeless (accessed on 20 Jan. 2021). The computer 16 may determine the position of the head H relative to the passenger compartment 12 based on a position of the head H identified in the image data. For example, the computer 16 may store a look-up table, formula, or the like that correlates positions of the head H identified in the image data (e.g., as pixel coordinate data) with actual positions within the passenger compartment 12 (e.g., as coordinates along the longitudinal axis A1 and/or the longitudinal axis A2). As another example, distance data from a proximity sensor fixed to one of the pillars may indicate a distance of the head H from the right side 20 or the left side 22.

Figure 3:
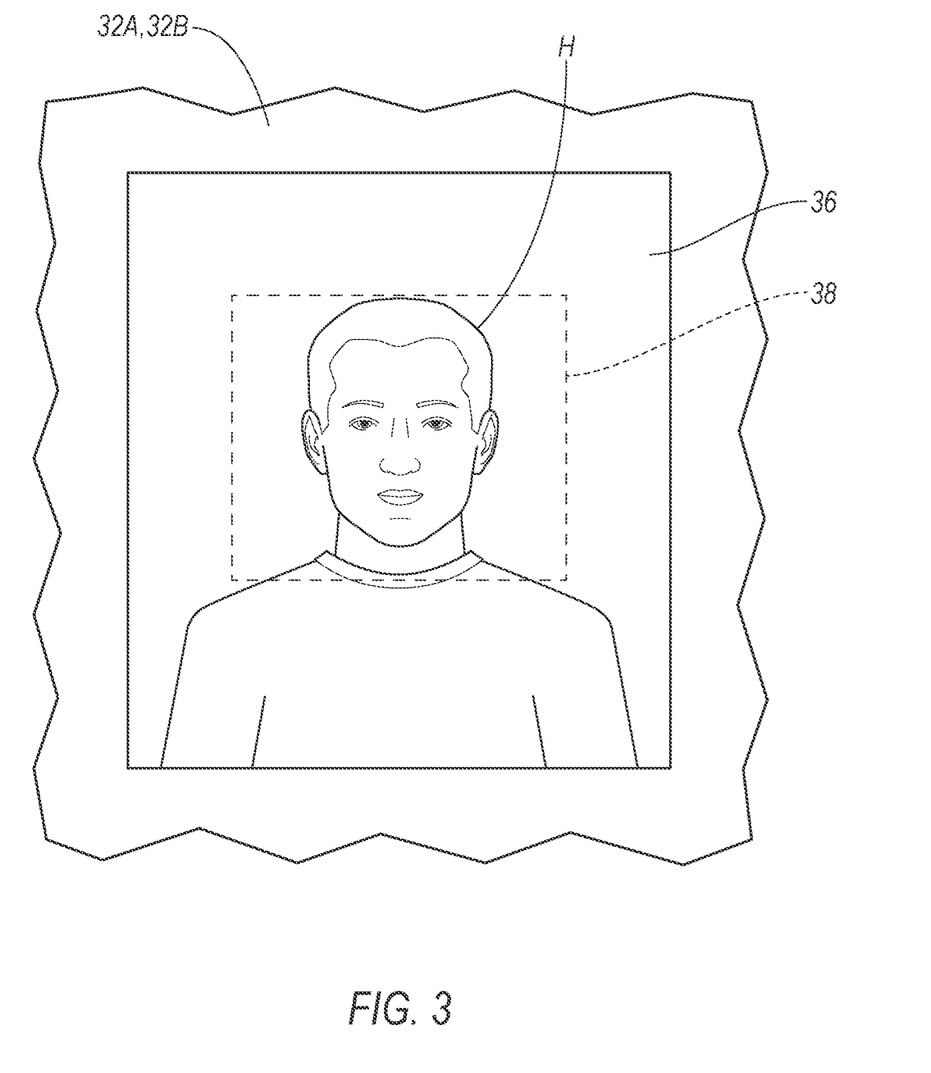
FIG. 3 is an illustration of a human machine interface (HMI) of the system.

The computer 16 is programmed to conduct a hearing test. The hearing test provides results that indicate an ability (or deficiency) of ears of the occupant to perceive various amplitudes (i.e., volumes) and frequencies (i.e., pitches) of sound. The hearing test may be a "pure tone" type test. For example, the computer 16 may command one or more of the speakers 28RF, 28RR, 28LF, 28LR to output a series of sounds at progressively increasing amplitudes and at various frequencies, e.g., between 125 Hz-8 kHz. The sound may be output at the right side 20 and not the left side 22, and vice versa. While the sound is being output the computer 16 may command the HMI 32A, 32B to output an indication requesting feedback from the occupant, e.g., the computer 16 may command a screen 36 of the HMI 32A, 32B to display text specifying that input is needed when the occupant perceives the sound. The occupant may provide an input to the HMI 32A, 32B when the sound is perceived, e.g., via a touch screen, steering wheel buttons, etc. The input from the occupant may specify whether the sound is perceived from the right side 20 or the left side 22. The computer 16 may store the results of the hearing test, e.g., which amplitudes and frequencies of sound the occupant indicated perceiving from the right side 20 and/or the left side 22. The stored results may include a time and date at which the test results were generated. The computer 16 may associate the results of the hearing test with an occupant profile that includes information about the occupant. The computer 16 may select which occupant profile to associate the results of the hearing test with from among a plurality occupant profiles by receiving information from the HMI 32A, 32B (e.g., indicating the occupant has selected a specific occupant profile), by establishing a connection with a certain key fob, smart phone, or other electronic device, or with other conventional structure and methods.

The computer 16 is programmed to conduct the hearing test based on the position of the head H of the occupant, e.g., as detected by the sensor 30. The computer 16 may conduct the hearing test, for example, in response to receiving data from the HMI 32A, 32B indicating the occupant has requested the hearing test, upon initial setup of a new occupant profile, and/or after a predetermined amount of time (e.g., 6 months) has lapsed since previously conducting the hearing test.

The computer 16 may conduct the hearing test based on the position of the head H using specified amplitudes for the hearing testing that are determined based on the position of the head H. Conducting the hearing test based on the position of the head H enables compensation for a distance between the head H of the occupant and the various speakers 28RF, 28RR, 28LF, 28LR, e.g., when testing with sound generated from a specific one of the sides and such that the amplitude generated by the speakers 28RF, 28RR, at the right side 20 or the speakers 28LF, 28LR at the left side 22 can perceived at the position of the head H at a certain amplitude. Conducting the hearing test based on the position of the head H enables the sound generated by the speakers 28RF, 28RR, 28LF, 28LR to be balanced at the head H position, e.g., such that the sound perceived at the position of the head H is similar from each of the speakers 28RF, 28RR, 28LF, 28LR.

As one example, when the hearing test is being conducted at the right side 20, the computer 16 may select an amplitude of sound for generation by the speakers 28RF, 28RR at the right side 20 based on a distance between the right side 20 and the position of the head H of the occupant. Similarly, when the hearing test is being conducted at the left side 22, the computer 16 may select an amplitude of sound for generation by the speakers 28LF, 28LR at the left side 22 based on a distance between the left side 22 and the position of the head H of the occupant, e.g., according to a formula or table as described below. The amplitude of the sound generated for the hearing test by the speakers 28RF, 28RR at the right side 20 may be relatively lower when the head H is relatively closer to such speakers 28RF, 28RR and relatively higher when the head H is relatively farther from such speakers 28RF, 28RR. Similarly, the amplitude of the sound generated for the hearing test by the speakers 28LF, 28LR at the left side 22 may be relatively lower when the head H is relatively closer to such speakers 28LF, 28LR and relatively higher when the head H is relatively farther from such speakers 28LF, 28LR.

As another example, when conducting the hearing test with the speakers 28RF, 28RR, 28LF, 28LR at the right side 20 and the left side 22, the computer 16 may select various amplitudes for the speakers 28RF, 28RR, 28LF, 28LR such that the amplitude of sound from the speakers 28RF, 28RR, 28LF, 28LR is perceived at the position of the head H to be generally the same. For example, the computer 16 may select, based on the position of the head H, a first amplitude and a second amplitude of sound that are different from each other. During the hearing test, the computer 16 may output sound at the first amplitude with the speakers 28RF, 28RR on the right side 20 of the passenger compartment 12 and sound at the second amplitude with speakers 28LF, 28LR at the left side 22 of the compartment. As the position of the head H moves away from the right side 20 and toward the left side 22 the first amplitude is relatively increased, and the second amplitude is relatively decreased. Conversely, as the position of the head H moves towards the right side 20 and away from the left side 22, the first amplitude is relatively decreased, and the second amplitude is relatively increased.

The computer 16 may select amplitudes for the hearing test with a look up table, formula, or the like that associates various distances from the right side 20 and/or the left side 22 with various amplitudes, and/or associates various positions along the cross-vehicle axis A2 with various first amplitudes and second amplitudes. The look-up table, the formula, etc., provide selected amplitudes that increase along with an increase in distance from the respective side. The look-up table, the formula, etc., provide selected first and second amplitudes that balance the sound at the position of the head H. The look up table, formula, or the like may be populated, derived, or otherwise determined based on empirical testing, computer modeling, and/or other analysis of sound within the passenger compartment 12. For example, sound may be output at a specified amplitude by one of the speakers 28RF, 28RR, 28LF, 28LR and decibel levels of such sound at various positions within the passenger compartment 12 may then be measured. compartment 12. As another example, decibel levels at various locations may be measured while an amplitude of the sound output by one of the speakers 28RF, 28RR, 28LF, 28LR is varied. The measured decibel levels indicate perceptible amplitudes of the sound at the various positions when output at the various amplitudes. Differences between the known amplitude of the sound as output and the decibel levels measured at the various positions indicates a relationship of the respective distances between the speakers 28RF, 28RR, 28LF, 28LR and the various measurement positions, taking into account acoustical properties of the passenger compartment 12. The amplitudes in a look up table, or determined from a formula, or the like can account for the distance of a speaker 28RF, 28RR, 28LF, 28LR taking into account acoustical properties of a cabin in which the speaker 28RF, 28RR, 28LF, 28LR is located. For example, the field of audiology can provide amplitudes appropriate for evaluating hearing, and such amplitudes may be adjusted, i.e., increased or decreased, for inclusion in a lookup table based on the differences between the known amplitude of the sound as output and the decibel levels measured at the various positions such that an occupant with a head H at one of the various positions perceives sound output by the speakers as the amplitudes provided by the audiologist. Alternatively or additionally, a formula may be derived using the amplitudes provided by the audiologist and based on the differences between the known amplitude of the sound as output and the decibel levels measured at the various positions such that the occupant with the head H at one of the various positions perceives sound output by the speakers as the known amplitudes.

The computer 16 may conduct the hearing test based on the position of the head H by conducting the hearing test while the position of the head H matches a specified head position. The specified position may be prestored in memory, e.g., generally centered relative to the seat supporting the occupant and along the cross-vehicle axis A2. The specified position may be the detected position of the head H at initiation of the hearing test, e.g., as detected by the occupant sensor. The computer 16 may command the speakers 28RF, 28RR, 28LF, 28LR to generate sound for the hearing test while the head H is at the specified position, and may control the speakers 28RF, 28RR, 28LF, 28LR such that sound for the hearing test is not generated while the head H is spaced from the specified position. In other words, the computer 16 may only initiate the hearing test when the head H is at the specified position, and/or may pause the hear test when the head H is not at the specified position and then resume when the head H is at the specified position.

To assist the occupant in placing their head H at the specified position, the computer 16 may display, via the HMI 32A, 32B in the vehicle 14, an indication of the detected position of the head H and the specified position of the head H. For example, and as shown in FIG. 3, the computer 16 may command the screen 36 of the HMI 32A, 32B to display the head H of the occupant as captured by a camera and an outline 38 indicating the specified head position. The occupant may then move their head H to be within the outline 38.

The computer 16 may be programmed to determine an ambient noise level in the passenger compartment 12, i.e., a level of noise (e.g., typically specified as a combination of frequency and amplitude, e.g., in Hertz and decibels) in the passenger compartment 12 other than from sound generated for the hearing test. The computer 16 may determine the ambient noise level based on data from one or more of the sensors 30, e.g., data from a microphone or pressure transducer may indicate the ambient noise level while the speakers 28RF, 28RR, 28LF, 28LR are not generating sound for the hearing test. The computer 16 may determine the ambient noise level with an estimation based on a speed of the vehicle 14, e.g., as detected by the sensors 30. For example, the computer 16 may store a look up table, formula, or the like that associates various vehicle speeds with ambient noise levels. The look up table, formula, etc., may be determined based on empirical testing, e.g., measuring and storing a level of detected ambient noise in the passenger compartment 12 at various speeds of the vehicle 14.

The computer 16 may be programmed to determine whether the ambient noise level is below a first predetermined threshold. The first predetermined threshold is set such that ambient noise at a level below the first predetermined threshold is unlikely to interfere with the hearing test. For example, ambient sound above the first predetermined threshold may interfere with sound generated by the speakers 28RF, 28RR, 28LF, 28LR for the hearing test and result in relatively less accurate results. The computer 16 may determine whether the ambient noise level is below the first predetermined threshold by comparing such values with each other. For example, the computer 16 may compare data from the microphone indicating the level of ambient noise with the first predetermined threshold. The computer 16 may conduct the hearing test after determining the ambient noise level in the passenger compartment 12 is below the first predetermined threshold.

The computer 16 may be programmed to determine whether the ambient noise level is below a second predetermined threshold for a specified amount of time. The second predetermined threshold and specified time are set such that exposure the ambient sound above the second predetermined for the specified amount of time is likely to degrade the occupant's ability to perceive sounds. For example, results for a hearing test conducted on the occupant directly after being exposed to ambient noise at the second predetermined threshold for the specified amount of time may be inaccurate and indicate degraded hearing compared to results of a hearing test conducted when such occupant has not been exposed to ambient noise at the second predetermined threshold for the specified amount of time.

The first threshold, the second threshold, and the specified amount of time may be empirically determined. For example, results of various hearing tests conducted with various levels of ambient noise and/or with occupants exposed to various levels of ambient noise for various lengths of time before taking the hearing tests may be compared to results of hearing test conducted without exposure to such ambient noise. The comparison may indicate what level of ambient noise, and/or, what length of time of exposure to ambient noise, interferes with obtaining accurate results with the hearing test.

The computer 16 may be programmed to actuate the speakers 28RF, 28RR, 28LF, 28LR, the HMI 32A, 32B, etc., to output sounds at specified frequencies and/or amplitudes based on the results of the hearing test. For example, the results of the hearing test may indicate that the occupant is relatively more likely to perceive sound at a first frequency and relatively less likely to perceive sound at a second frequency. The computer 16 may actuate the speakers 28RF, 28RR, 28LF, 28LR, the HMI 32A, 32B, etc., to output sounds at the first frequency identified by the test to be more likely perceptible by the occupant, e.g., to notify the occupant that a fuel reserve is low, that a check engine light has illuminated, that air pressure in a tire of the vehicle 14 may be low, etc.

The computer 16 may be programmed to limit an amplitude of sound output in the passenger compartment 12 based on the results of the hearing test. The computer 16 may limit a maximum amplitude of sound output by the speakers 28RF, 28RR, 28LF, 28LR, the HMI 32A, 32B, etc., by commanding only the speakers 28RF, 28RR, 28LF, 28LR, the HMI 32A, 32B, etc., to generate sounds below the maximum amplitude. For example, results of one or more of the hearing test may indicate hearing loss of the occupant, e.g., the results may indicate that the occupant does not perceive certain frequencies of sounds at amplitudes that are typically perceivable by a human and/or that the perceptibility of certain frequencies of sound by the occupant has degraded across multiple hearing tests. When the results indicate hearing loss, limiting the amplitude of the sound to below the maximum amplitude may reduce a rate of such hearing loss of the occupant. The maximum amplitude may be determined by standard audiology techniques, e.g., indicating what levels of amplitude of sounds are either unlikely or likely to contribute to hearing loss. The computer 16 may limit amplitude at specific frequencies. For example, the results of the hearing test may indicate that the occupant only has difficulty perceiving certain frequencies of sounds. In such case, the computer 16 may limit the amplitude of sound generated at those certain frequencies.

The computer 16 may be programed to notify the occupant when results of a plurality of hearing tests, e.g., stored in memory and associated with the occupant's user profile, indicate deterioration of hearing of the occupant. The computer 16 may determine whether the results of the plurality of hearing test indicate hearing deterioration by comparing results of respective hearing tests with each other. For example, the computer 16 may determine that hearing of the occupant has deteriorated when the likelihood of perception of sounds at various frequencies and amplitudes is shown by the results to have decreased over time. The computer 16 may indicate such deterioration of hearing to the occupant, e.g., by commanding the screen 36 of the HMI 32A, 32B to display such information, by sending a message to an email address associated with the user profile, etc.

Figure 4:
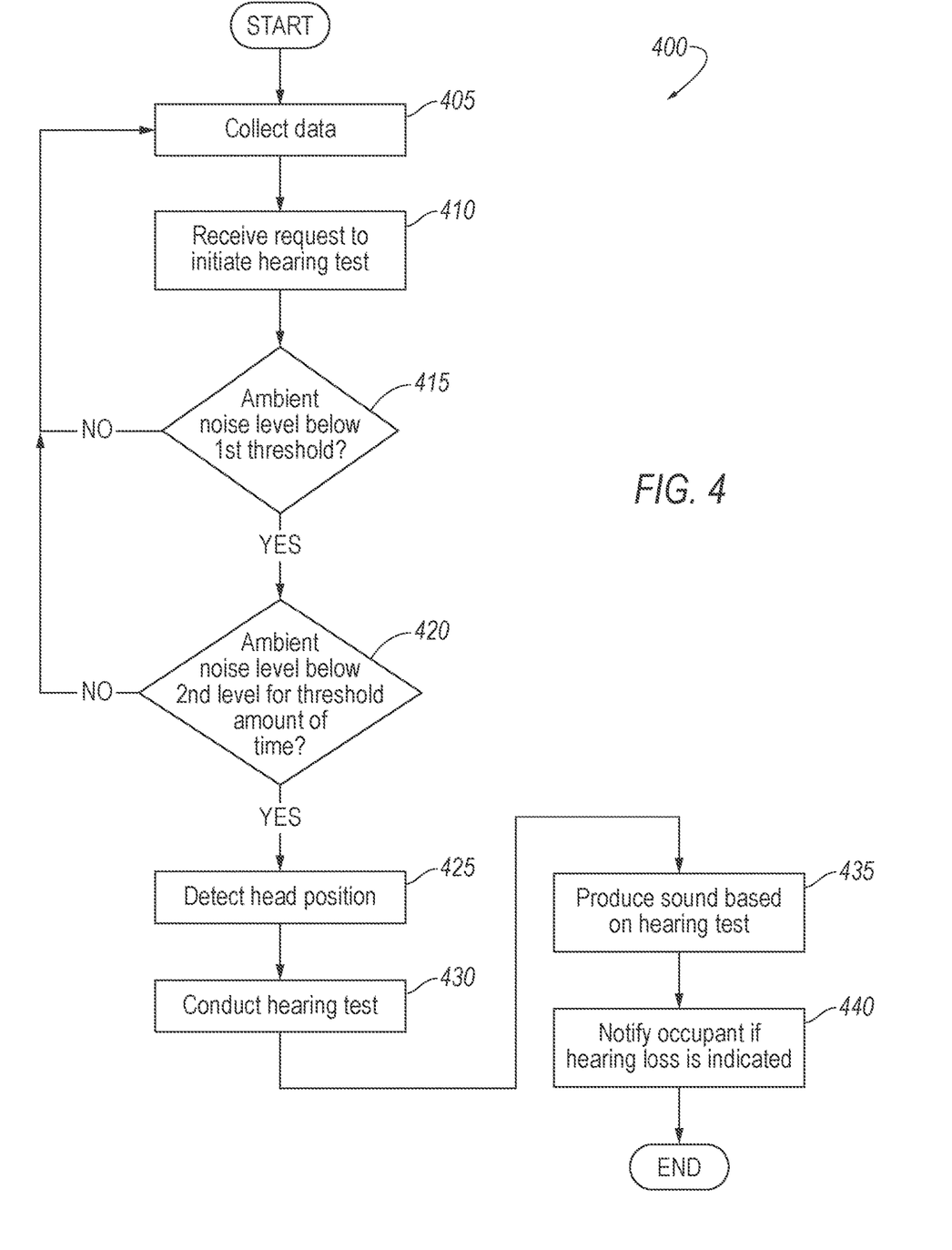
FIG. 4 is a flow chart illustrating a process for conducting the hearing test.

FIG. 4 shows a process flow diagram illustrating an exemplary process 400 for operating the system 10. The process 400 begins in a block 405 in which the computer 16 collects data, e.g., received from the sensors 30, the HMI 32A, 32B, etc. The computer 16 may receive data substantially continuously or at intervals, e.g., periodically such as every 100 milliseconds. The computer 16 may store the data, e.g., in memory.

At a block 410 the computer 16 receives a request to initiate a hearing test, e.g., from the HMI 32A, 32B, via the communication network. The HMI 32A, 32B may send the request to the computer 16 in response to receiving input, e.g., by the occupant. Alternatively or additionally, the computer 16 may include and could execute programming to determine to initiate a hearing test, e.g., based on an amount of time since the previous hearing test, etc.

Next at a block 415 the computer 16 determines whether an ambient noise level in the passenger compartment 12 is below a first predetermined threshold, e.g., based on data from one or more sensors 30 such as a microphone. The first predetermined threshold is set such that ambient noise at a level below the first predetermined threshold is unlikely to interfere with the hearing test, e.g., as described herein. In response to determining the ambient noise in the passenger compartment 12 is not below the first predetermined threshold the computer 16 may command the HMI 32A, 32B to indicate that the ambient noise level is too high for conducting a hearing test and return to the block 405. In response to determining the ambient noise in the passenger compartment 12 is below the first predetermined threshold, the computer 16 may move to a block 420.

At the block 420 the computer 16 determines whether the ambient noise level in the passenger compartment 12 has been below a second predetermined threshold for a specified amount of time, e.g., with data from the microphone, with an estimate the based on a speed of the vehicle 14, etc. The second predetermined threshold and specified amount of time may be set such that exposure to the ambient sound above the second predetermined for the specified amount of time is likely to degrade the occupant's ability to perceive sound, e.g., as described herein. In response to determining the ambient noise level in the passenger compartment 12 has not been below the second predetermined threshold for the specified amount of time, the computer 16 may command the HMI 32A, 32B to indicate to the user that the ambient noise level has been too high for too long to conduct the test and the computer 16 may return to the block 405. In response to determining the ambient noise level in the passenger compartment 12 has been below the second predetermined threshold for the specified amount of time, the computer 16 may move to a block 425.

At the block 425 the computer 16 detects a position, e.g., an initial position, of the head H of an occupant within the passenger compartment 12 of the vehicle 14, e.g., based on data from one or more of the sensors 30, such as data from an occupant sensor, and as described herein. The computer 16 may, for example, detect a distance from the head H to the right side 20 and/or the left side 22, a position of the head H along the cross-vehicle axis A2 and/or the longitudinal axis A1, etc. The computer may store the detected position of the head in memory.

Next at a block 430 the computer 16 conducts a hearing test based on the position of the head H of the occupant detected at the block 425. For example, the computer 16 may select various amplitudes for the speakers 28RF, 28RR, 28LF, 28LR such that the amplitude of sound from the speakers 28RF, 28RR, 28LF, 28LR is perceived at the position of the head H to be generally the same. As another example, the computer 16 may select an amplitude of sound for generation by the speakers 28RF, 28RR at the right side 20 based on a distance between the right side 20 and the position of the head H of the occupant. The computer 16 may select the amplitudes with a look up table, formula, or the like, e.g., as described herein. After selecting the amplitudes, the computer 16 command one or more of the speakers 28RF, 28RR, 28LF, 28LR to output a series of sounds at the selected amplitudes (e.g., the computer 16 may conduct a "pure type" type test with the selected amplitudes). The computer 16 may command the screen 36 of the HMI 32A, 32B to display text specifying that input is needed when the occupant perceives the sound at the selected amplitudes while such sounds are output. The computer 16 may receive, e.g., from the HMI 32A, 32B, indicating that the sounds have been perceived by the occupant.

The computer may continue to conduct the hearing test only while the position of the head H matches a specified head position. The specified head position may be the initial position of the head detected at the block 425. For example, the computer 16 may continue to detect the head position while conducting the hearing test, e.g., substantially continuously or at intervals such that the computer 16 receives a generally current position of the head, and may compare the current position with the specified head position. Upon determining that the current head position and the specified head position match, the computer 16 may continue to generate sounds for the hearing test. Upon determined the current head position and the specified head position do not match, the computer 16 may pause generation of sound for the hearing test, resuming when the current position matches the specified position. To assist the occupant in maintaining their head H at the specified head position while conducting the hearing test, the computer may display the position of the head H and the specified head position to the occupant, e.g., as an image of the head H and an outline 38 indicating the specified head position on the screen 36 of the HMI 32A, 32B, as illustrated in FIG. 3. The computer may associate the results of the hearing test with a profile of the occupant and save the results and association in memory.

At a block 435, the computer may output sound at least at one of a specified frequency or amplitude, the specified frequency and/or amplitude selected based on results of the hearing test conducted at the block 430, e.g., by commanding one or more of the speakers 28RF, 28RR, 28LF, 28LR to generates sound at such frequency and/or amplitude. For example, the computer 16 may command the speakers 28RF, 28RR, 28LF, 28LR to generate sound at a certain frequency to alert the occupant and/or may limit a maximum amplitude of the sound generated in the passenger compartment 12, e.g., as described herein.

At a block 440, the computer may to notify the occupant when the results of the hearing test conducted at the block 430 and results of one or more previously conducted and stored hearing tests indicate deterioration of hearing of the occupant, e.g., as described herein. The computer may, for example, notify the occupant via the HMI 32A, 32B.

In the drawings, the same reference numbers indicate the same elements. Further, some or all of these elements could be changed. With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Computer executable instructions may be compiled or interpreted from computer programs created using a variety of programming languages and/or technologies, including, without limitation, and either alone or in combination, Java™, C, C++, Visual Basic, Java Script, Perl, HTML, etc. In general, a processor (e.g., a microprocessor) receives instructions, e.g., from a memory, a computer readable medium, etc., and executes these instructions, thereby performing one or more processes, including one or more of the processes described herein. Such instructions and other data may be stored and transmitted using a variety of computer readable media. A file in a networked device is generally a collection of data stored on a computer readable medium, such as a storage medium, a random access memory, etc.

A computer readable medium includes any medium that participates in providing data (e.g., instructions), which may be read by a computer. Such a medium may take many forms, including, but not limited to, non volatile media, volatile media, etc. Non volatile media include, for example, optical or magnetic disks and other persistent memory. Volatile media include dynamic random access memory (DRAM), which typically constitutes a main memory. Common forms of computer readable media include, for example, a floppy disk, a flexible disk, hard disk, magnetic tape, any other magnetic medium, a CD ROM, DVD, any other optical medium, punch cards, paper tape, any other physical medium with patterns of holes, a RAM, a PROM, an EPROM, a FLASH EEPROM, any other memory chip or cartridge, or any other medium from which a computer can read.

Use of "in response to," "based on," and "upon determining" herein indicates a causal relationship, not merely a temporal relationship.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

What is claimed is:

1. A system, comprising a computer including a processor and a memory storing instructions executable by the processor to:
    detect a position of a head of an occupant within a passenger compartment of a vehicle;
    conduct a hearing test based on the position of the head of the occupant; and
    output sound at least at one of a specified frequency or amplitude, the specified frequency or amplitude selected based on results of the hearing test.

2. The system of claim 1, wherein the instructions further include instructions to select a first amplitude of sound for conducting the hearing test, the first amplitude of sound being determined based on the position of the head.

3. The system of claim 2, wherein the instructions further include instructions to select a second amplitude of sound for conducting the hearing test, the second amplitude of sound being determined based on the position of the head and different than the first amplitude of sound.

4. The system of claim 3, wherein the instructions further include instructions to output the first amplitude of sound at a right side of the passenger compartment and the second amplitude of sound at a left side of the passenger compartment.

5. The system of claim 1, wherein the instructions further include instructions to display, via a human machine interface in the vehicle, the position of the head and a specified head position, and to conduct the hearing test while the position of the head matches the specified head position.

6. The system of claim 1, wherein the instructions further include instructions to conduct the hearing test while the position of the head matches a specified head position.

7. The system of claim 1, where the instructions further include instructions to detect the position of the head based on data from a camera.

8. The system of claim 1, where the instructions further include instructions to conduct the hearing test in response to determining an ambient noise level in the passenger compartment is below a predetermined threshold.

9. The system of claim 1, where the instructions further include instructions to conduct the hearing test in response to determining an ambient noise level in the passenger compartment has been below a predetermined threshold for a specified amount of time.

10. The system of claim 9, where the instructions further include instructions to estimate the ambient noise level in the passenger compartment based on a speed of the vehicle.

11. The system of claim 1, where the instructions further include instructions to store results of a plurality of hearing tests and to notify the occupant when the results of the plurality of hearing tests indicate deterioration of hearing of the occupant.

12. The system of claim 1, where the instructions further include instructions to limit an amplitude of sound output in the passenger compartment based on the results of the hearing test.

13. The system of claim 1, where the instructions further include instructions to store and associate the results of the hearing test with a profile of the occupant.

14. A method, comprising:
    detecting a position of a head of an occupant along a cross-vehicle axis within a passenger compartment of a vehicle;
    conducting a hearing test based on the position of the head of the occupant along the cross-vehicle axis; and
    outputting sound at least at one of a specified frequency or amplitude, the specified frequency or amplitude selected based on results of the hearing test.

15. The method of claim 14, further comprising selecting a first amplitude of sound for use while conducting the hearing test, the first amplitude of sound determined based on the position of the head.

16. The method of claim 15, further comprising selecting a second amplitude of sound for use while conducting the hearing test, the second amplitude of sound determined based on the position of the head and different than the first amplitude of sound.

17. The method of claim 16, further comprising outputting the first amplitude of sound at a right side of the passenger compartment and the second amplitude of sound at a left side of the compartment.

18. The method of claim 14, further comprising conducting the hearing test while the position of the head matches a specified head position.

19. The method of claim 14, further comprising conducting the hearing test after determining an ambient noise level in the passenger compartment has been below a predetermined threshold for a specified amount of time.

20. The method of claim 14, further comprising storing results of a plurality of hearing tests and to notify the occupant when the results of the plurality of hearing tests indicate deterioration of hearing of the occupant.

* * * * *